United States Patent [19]
Webster et al.

[11] Patent Number: 5,503,320
[45] Date of Patent: Apr. 2, 1996

[54] SURGICAL APPARATUS WITH INDICATOR

[75] Inventors: John Webster, Cromwell; James R. Pratt, Wolcott, both of Conn.

[73] Assignee: United States Surgical Corporation, Norwalk, Conn.

[21] Appl. No.: 109,134

[22] Filed: Aug. 19, 1993

[51] Int. Cl.⁶ .................................................. A61B 17/068
[52] U.S. Cl. ..................... 227/176.1; 227/19; 600/103; 600/117
[58] Field of Search .............................. 227/19, 175, 179, 227/180, 176; 128/4

[56] References Cited

U.S. PATENT DOCUMENTS

| | | |
|---|---|---|
| 4,057,063 | 11/1977 | Gieles et al. . |
| 4,114,623 | 9/1978 | Meinke et al. . |
| 4,132,224 | 1/1979 | Randolph . |
| 4,168,707 | 9/1979 | Douvas et al. . |
| 4,188,927 | 2/1980 | Harris . |
| 4,213,463 | 7/1980 | Osenkarski . |
| 4,249,539 | 2/1981 | Vilkomerson et al. . |
| 4,261,360 | 4/1981 | Perez . |
| 4,346,717 | 8/1982 | Haerten . |
| 4,387,721 | 6/1983 | Enjoji . |
| 4,407,294 | 10/1983 | Vilkomerson . |
| 4,416,276 | 11/1983 | Newton et al. . |
| 4,416,277 | 11/1983 | Newton et al. . |
| 4,423,727 | 1/1984 | Widran et al. . |
| 4,437,464 | 3/1984 | Crow . |
| 4,478,217 | 10/1984 | Shimada et al. . |
| 4,494,541 | 1/1985 | Archibald . |
| 4,517,976 | 5/1985 | Murakoshi . |
| 4,519,391 | 5/1985 | Murakoshi . |
| 4,598,579 | 7/1986 | Cummings et al. . |
| 4,650,462 | 3/1987 | DeSatnick et al. . |
| 4,676,772 | 6/1987 | Hooven . |
| 4,685,459 | 8/1987 | Koch et al. . |
| 4,694,290 | 9/1987 | Schwarz . |
| 4,705,038 | 11/1987 | Sjostrom et al. . |
| 4,742,815 | 5/1988 | Ninan et al. . |
| 4,750,902 | 6/1988 | Wuchinich et al. . |
| 4,772,257 | 9/1988 | Hakim et al. . |
| 4,823,791 | 4/1989 | D'Amelio et al. . |
| 4,836,187 | 6/1989 | Iwakoshi et al. . |
| 4,902,277 | 2/1990 | Mathies et al. . |
| 4,909,782 | 3/1990 | Semm et al. . |
| 4,924,852 | 5/1990 | Suzuki et al. . |
| 4,930,494 | 6/1990 | Takehana et al. . |
| 4,932,394 | 6/1990 | Nanaumi . |
| 4,936,842 | 6/1990 | D'Amelio et al. . |
| 4,996,975 | 3/1991 | Nakamura . |
| 4,998,527 | 3/1991 | Meyer . |
| 5,006,109 | 4/1991 | Douglas et al. . |
| 5,029,583 | 7/1991 | Meserol et al. . |
| 5,047,046 | 9/1991 | Bodoia . |
| 5,050,610 | 9/1991 | Oaks et al. . |
| 5,078,714 | 1/1992 | Katims . |
| 5,080,104 | 1/1992 | Marks et al. . |
| 5,086,401 | 2/1992 | Glassman et al. . |
| 5,125,926 | 6/1992 | Rudko et al. . |
| 5,161,536 | 11/1992 | Vilkomerson et al. . |
| 5,161,543 | 11/1992 | Abramson . |
| 5,196,017 | 3/1993 | Silva et al. . |
| 5,201,325 | 4/1993 | McEwen et al. . |
| 5,215,523 | 6/1993 | Williams et al. . |

(List continued on next page.)

FOREIGN PATENT DOCUMENTS

| | | |
|---|---|---|
| 0067702 | 12/1982 | European Pat. Off. . |
| 0469966 | 2/1992 | European Pat. Off. . |
| 0524764 | 1/1993 | European Pat. Off. . |
| 0552050 | 7/1993 | European Pat. Off. . |
| 2569556 | 3/1986 | France . |
| 4213584 | 11/1992 | Germany . |
| 4136861 | 5/1993 | Germany . |
| 4206126 | 9/1993 | Germany . |
| WO91/03207 | 3/1991 | WIPO . |
| WO93/08757 | 5/1993 | WIPO . |

*Primary Examiner*—Scott A. Smith

[57] ABSTRACT

An apparatus and system are disclosed for indicating relative positions of elements in a surgical apparatus. The indicating elements can include electrical circuitry for activating visual, audible or tactile indicators, thereby alerting the user that an event has occured with respect to the instrument.

16 Claims, 12 Drawing Sheets

U.S. PATENT DOCUMENTS

| | | |
|---|---|---|
| 5,218,970 | 6/1993 | Turnbull et al. . |
| 5,230,338 | 7/1993 | Allen et al. . |
| 5,236,432 | 8/1993 | Matsen, III et al. . |
| 5,238,000 | 8/1993 | Niwa . |
| 5,239,997 | 8/1993 | Guarino et al. . |
| 5,240,007 | 8/1993 | Pytel et al. . |
| 5,240,008 | 8/1993 | Newell . |
| 5,246,419 | 9/1993 | Absten . |
| 5,246,422 | 9/1993 | Favre . |
| 5,247,932 | 9/1993 | Chung et al. . |
| 5,247,938 | 9/1993 | Silverstein et al. . |
| 5,247,939 | 9/1993 | Sjoquist et al. . |
| 5,249,579 | 10/1993 | Hobbs et al. . |
| 5,249,581 | 10/1993 | Horhal et al. . |
| 5,249,583 | 10/1993 | Mallahy . |
| 5,267,997 | 12/1993 | Farin et al. . |
| 5,268,622 | 12/1993 | Philipp . |
| 5,269,289 | 12/1993 | Takehana et al. . |
| 5,269,750 | 12/1993 | Grulke et al. . |
| 5,273,025 | 12/1993 | Sakiyama et al. . |

SURGICAL APPARATUS WITH INDICATOR

FIELD OF THE INVENTION

The present invention relates to surgical instruments, e.g., instruments for applying surgical fasteners or staples to body tissue, and more particularly relates to visual indicators for such devices.

BACKGROUND OF THE RELATED ART

Surgical fastening or stapling devices have been used in the medical industry for several years. Many of these instruments require approximation of various components during use. When applying surgical fasteners to bodily tissue, for example, various structures of the instrument must be within a predetermined distance in order for the device to properly function. In performing some surgical procedures, the surgeon may have difficulty in seeing the necessary components to determine when proper approximation has been achieved. Additionally, even when a surgeon can view the various components being approximated, proper gaps and/or distances may be so minute or precise, that even a trained eye may have difficulty in determining if proper approximation and/or alignment has been achieved.

There currently exist instruments which have color coded elements to inform the user of proper gaps between the components. However, these elements are typically formed in windows in the instruments and require the surgeon to take a close look to obtain the desired information.

Additionally, in laparoscopic surgery, the surgeon typically views the operation in a video screen, e.g., a TV monitor positioned remote from the surgical site. If the indicator is positioned on a handle portion of the instrument, the surgeon would need to look away from the video screen to view the indicator. If the indicator is positioned on the distal end of the instrument, then the indicator must be configured and colored so that it is readily viewable in the video screen, taking into account that the positioning of the instrument relative to the viewing scope may be less than optimum for viewing the indicator and that the illumination inside the body cavity may be limited.

Aside from surgical instrumentation that require approximation of various components during use, other surgical instruments are used in surgical procedures whereby such instruments assume multiple positions and orientations during the surgical procedure. For example, graspers, dissectors, scissors and the like assume open and closed configurations in response to actions by the surgeon. Other devices, e.g., electrocautery devices, lasers and the like, supply energy to the surgical site. When using such instrumentation, it is necessary that the surgeon appreciate the status of the instrument, e.g., open/closed, energized/non-energized, etc., to properly utilize the instrument and perform the surgical procedure.

Therefore, there is a need for improved indicators for surgical instruments which would provide appropriate information to the surgeon in a convenient and efficacious manner. For example, it is desirable for surgical instrumentation to include indicators that would inform surgeons that an event has occurred and/or provide information to the user that the instrument is properly aligned and/or approximated to perform a specific function.

SUMMARY OF THE INVENTION

The present invention provides novel visual indication means in association with one or more surgical instruments. Each surgical instrument can include a housing, a first member extending from the housing and a second member positioned in spaced relation relative to the first member, wherein at least one of the members is movable relative to the other. Means are positioned in the apparatus for visually, audibly or tactilely indicating movement of the one member to a predetermined position relative to the other member. The novel indicator means of the present invention includes a power source connected to the indicator means. In one embodiment, the indicator means includes a voltage source, i.e., a battery, a visual indicator which is responsive to electrical current, i.e., a light emitting diode ("LED"), and means for transporting electrical current from the voltage source to the visual indicator. Contacts within the instrument are positioned such that an electrical circuit is open, i.e., the visual indicator is inactive, in one position and closed, i.e., the visual indicator is activated, in another position.

In another embodiment of the invention, visual indication means are provided which generate a visual indication at a location remote from the surgical instrument to which the visual indication relates. For example, in laparoscopic or endoscopic surgery, surgical instrumentation is utilized such that the surgery may be performed in a minimally invasive manner. In such procedures, the surgeon typically views the movements and actions of the surgical instrumentation on a video monitor positioned in the operating room, the image being delivered to the monitor by cooperating equipment which includes a rigid or flexible endoscope/laparoscope, a light source delivered to the operative site, a camera adapter associated with the endoscope/laparoscope and appropriate transmission cables and the like. According to the present invention, surgical instrumentation to be utilized in the laparoscopic/endoscopic procedure are provided with visual indication means which sense the relative position or condition of the instrument and, through transmission cables and the like, transfer data concerning the position/condition of the instrument to the video monitor. The data is preferably displayed in the form of an icon, symbol or like means, e.g., changes in color, form or position of data displayed on the monitor, which readily communicates to the surgeon relevant information concerning the position/condition of the subject surgical instrumentation.

BRIEF DESCRIPTION OF THE DRAWINGS

The foregoing features of the present invention will become more readily apparent and may be understood by referring to the following detailed description of illustrative embodiments of the invention, taken in conjunction with the accompanying drawings, in which.

DETAILED DESCRIPTION OF THE PREFERRED EMBODIMENTS

Figure 1:
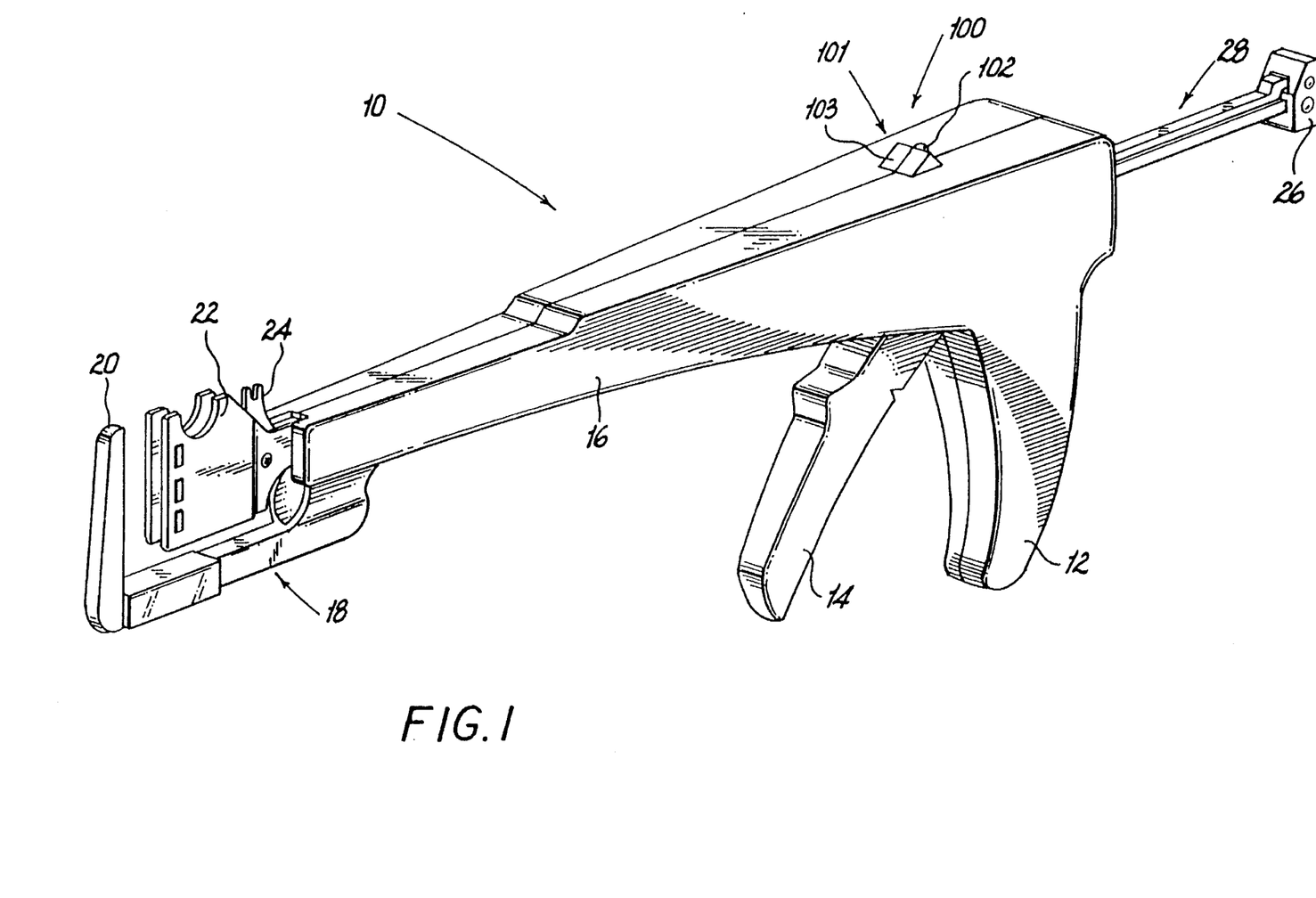
FIG. 1 illustrates a perspective view of a surgical fastening instrument for applying linear rows of fasteners including one embodiment of the indicator mechanism of the present invention.

Referring now in specific detail to the drawings, in which like reference numerals identify similar or identical elements throughout the several views, FIG. 1 shows a surgical fastening instrument 10 which employs an adjustable closure mechanism and the visual indicator device 100 of the present invention. Fastening instrument 10 is provided with a stationary hand grip or hand rest 12 and an actuating handle 14. An elongated body portion 16 is provided which terminates in a distal jaw mechanism 18 which includes an anvil jaw 20 and a cartridge jaw 22. A fastener cartridge (not shown) is positioned within cartridge jaw 22 for driving staples or fasteners through tissue against an anvil surface positioned on anvil jaw 20. Alternatively, the cartridge can contain the fastener portions of two part fasteners which are driven into retainers positioned on the anvil jaw. At the handle end of instrument 10 is provided a push button 26 for operating an advancement mechanism 28, whose function will be described below. An external portion 101 of the visual indicator device includes housing 103 and visual indicator 102.

Figure 2:
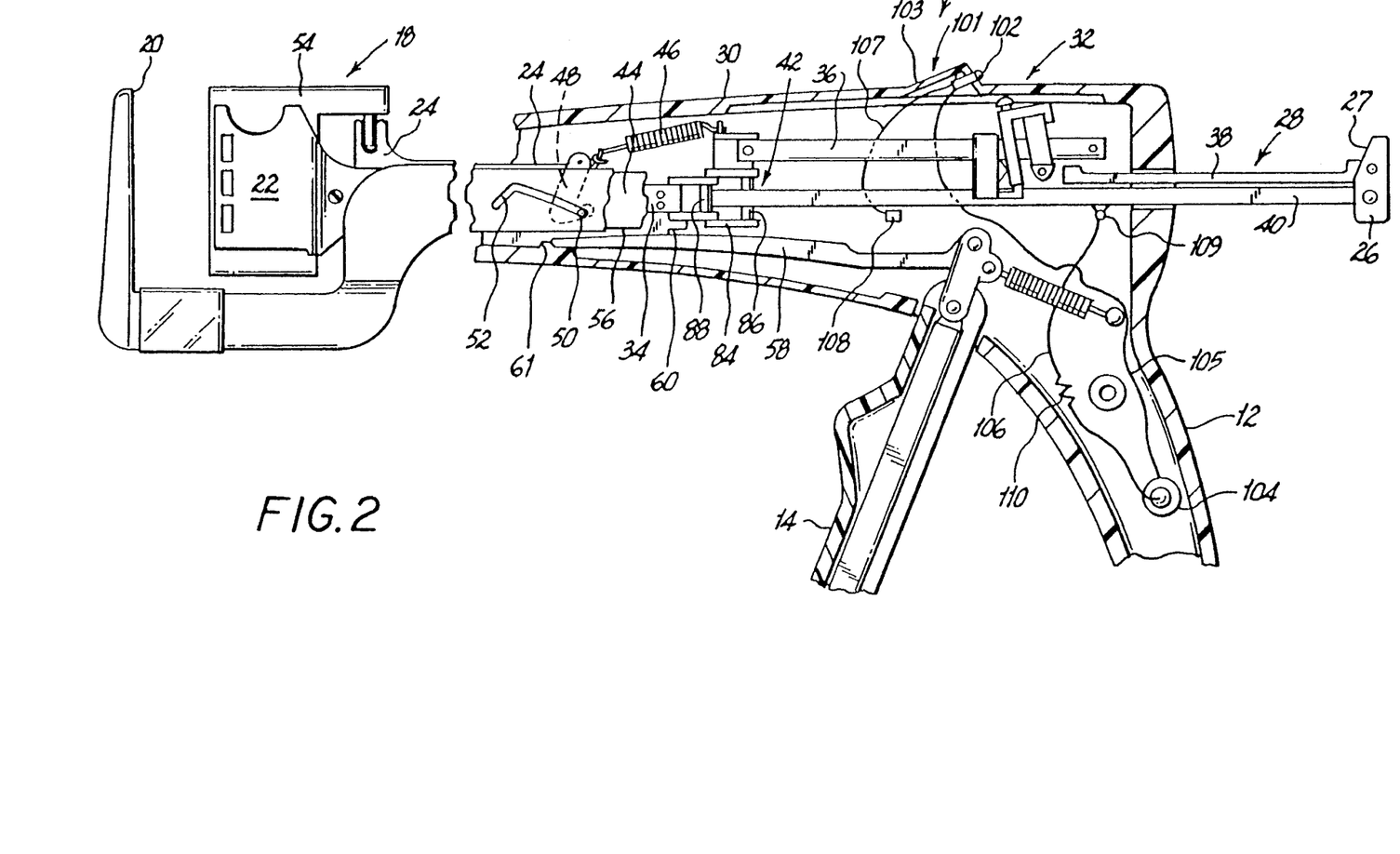
FIG. 2 illustrates a side cross-sectional plan view of a surgical fastening instrument of FIG. 1 in an open and at rest condition.

As seen in FIG. 2, push button 26 and advancing mechanism 28 extend outwardly from the proximal end of the instrument 10. A releasable retaining mechanism 32 is slidably engaged to the stationary rod member 36 and is coupled to slider mechanism 40 so that as slider mechanism 40 is urged forwardly into housing 30, retaining mechanism 32 is slidably retained along stationary rod member 36.

Advancing mechanism 28 comprises slider mechanism 40 and release rod member 38, such that release rod member 38 and slider mechanism 40 are secured to push button 26. Thrusting push button 26 towards housing 30 slides release rod 38 and slider mechanism 40 into the housing to move the retaining mechanism 32 along rod 36. Slider mechanism 40 extends to linkage structure 42 to activate the linkage structure 42 and urge jaw mechanism 18 distally. Linkage structure 42 moves movable rod 34, as well as fastener driver 56, cartridge frame 44, alignment pin advancement means 24, and cartridge 54 all in a distal direction to selectively position movable cartridge jaw 22 and stationary anvil jaw 20. A more detailed description of the individual mechanisms of the adjustable closure component is described in commonly assigned pending U.S. application Ser. No. 07/779,505 filed Oct. 18, 1991, which is incorporated herein by reference.

Turning to the light indicator mechanism 100 of the present invention, with reference to FIG. 2, an electrical circuit is disposed within the surgical instrument. Electrical contact 109 is fixedly positioned on slider mechanism 40. Visual indicator 102 is in the form of an LED and is disposed in housing 103. While visual indicator 102 is preferably an LED, other devices which emit a detectable response to an electrical current are considered to be within the scope of the invention, i.e., incandescent lamps, liquid crystal displays (LCD's), audible indicators, tactile indicators and light/temperature responsive materials. The electrical circuit includes wires 105, 106 and 107. Wire 105 electrically connects indicator 102 to a voltage source 104, such as a battery, wire 106 connects the voltage source 104 to contact 109, and wire 107 connects indicator 102 to contact 108. Clearly, alternatively, a single wire or any number of wires can be used to electrically connect these components. Illumination of indicator 102 is accomplished by closing the circuit which is achieved by bringing contact 109 into abutment with contact 108 as described hereinbelow. Optionally, a current limiter, i.e., a resistor, may be disposed within the electrical circuit. Current limiter 110 is shown on wire 106.

Referring now to FIGS. 2 through 5, the operation of the surgical fastener apparatus 10 having the visual indicator 100 of the present invention will now be described.

Tissue is first inserted between cartridge jaw 22 and anvil jaw 20 when the instrument is in the position shown in FIG. 2. In this position, contacts 108 and 109 are spaced apart so that the circuit is not complete and indicator 102 is inactive.

Figure 3:
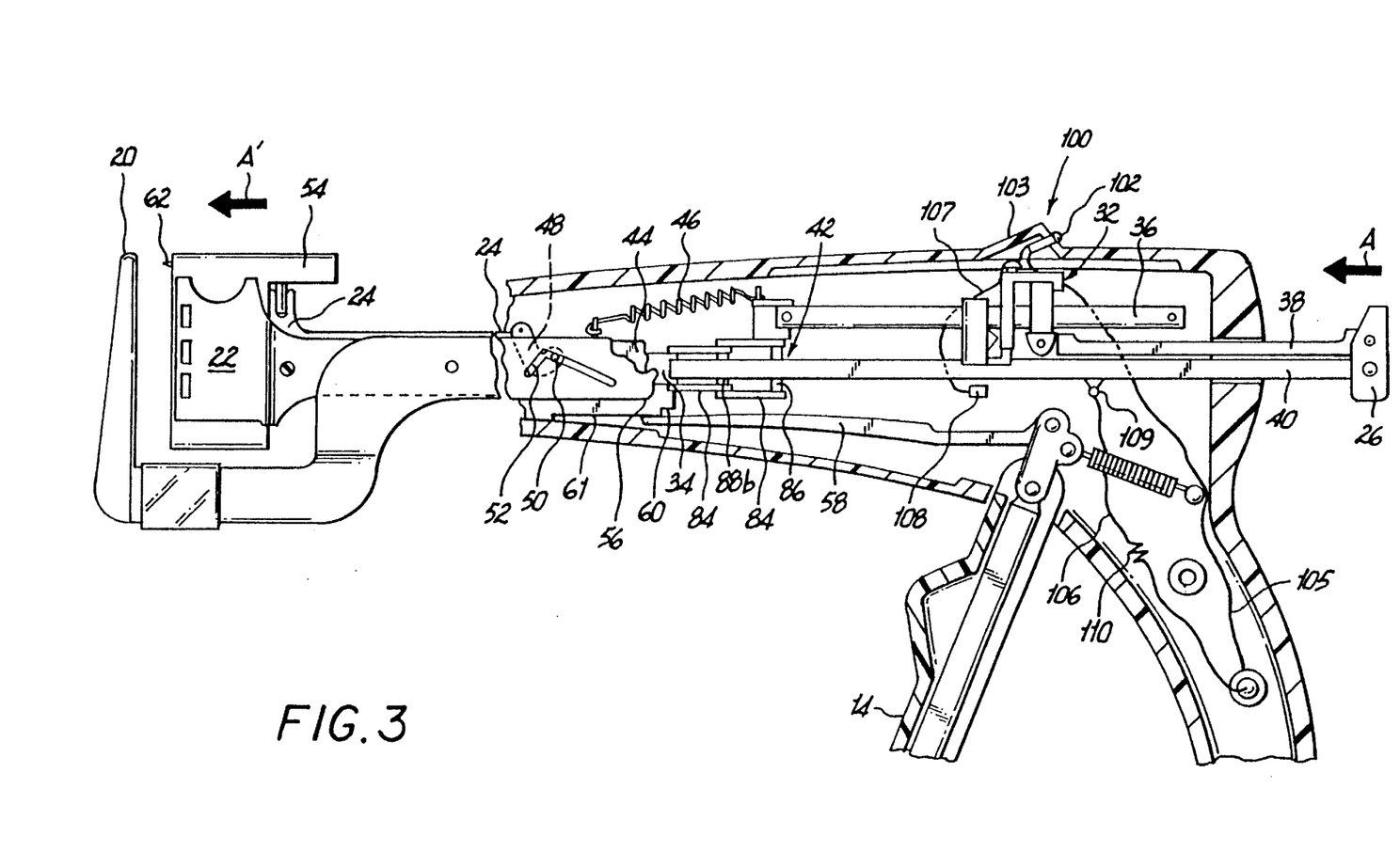
FIG. 3 illustrates the device of FIG. 2 in which the jaw mechanism is partially closed, and the indicator mechanism remains inactivated.

After tissue which is to be surgically repaired is positioned between cartridge jaw 22 and anvil jaw 20, push button 26 is pushed in the direction of arrow A as seen in FIG. 3 which moves slider mechanism 40 and release rod 38 into housing 30. Retaining mechanism 32 is slid distally along stationary rod 36, and camming surface 90 of slider mechanism 40 engages stationary post 88b to deploy linkage structure 42. As linkage structure 42 is deployed, movable rod 34 is urged forwardly along with cartridge frame 44, thus urging driving pin 50 along frame track 52. Distal movement of slider mechanism 40 carries contact 109 distally toward contact 108. The force of biasing spring 46 is overcome as push button 26 is urged in the direction of arrow A.

As driving pin 50 moves in track 52, driving link 48 is moved to the position shown in FIG. 3, which urges alignment pin advancement means 24 to the position shown at the jaw mechanism 18. In this position, alignment pin 62 protrudes from cartridge 54 and aligns with the alignment hole in anvil jaw 20 as cartridge 54 moves in the direction of arrow A'.

As linkage structure 42 is deployed and movable rod 34 and cartridge frame 44 move distally, fastener driver 56 also moves distally and coupling arm 58 slides along bearing surface 61.

Figure 4:
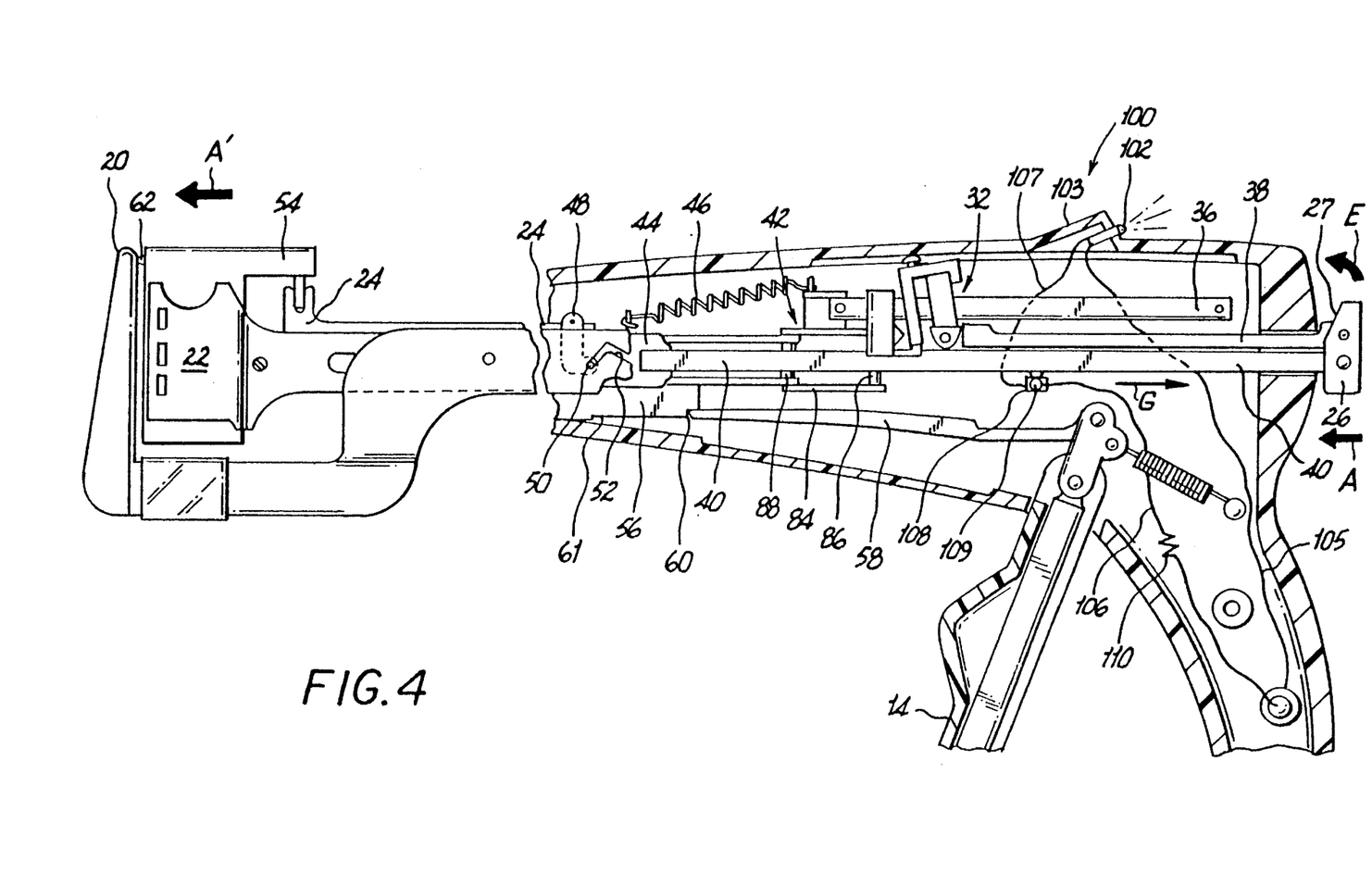
FIG. 4 illustrates the device of FIG. 2 in which the jaw mechanism is fully closed and the indicator mechanism is activated.

When push button 26 is fully actuated, linkage structure 42 is fully deployed as shown in FIG. 4, and retaining mechanism 32 frictionally engages stationary rod 36 to maintain instrument 10 in the position shown in FIG. 4. At this time, cartridge 54 has moved into position in the direction of arrow A' so that alignment pin 62 is positioned in the alignment hole in anvil jaw 20. Alignment pin advancement means 24 moves slightly proximally so that alignment pin 62 does not protrude beyond anvil jaw 20, and driving link 48 assumes the position shown in FIG. 4. Driving pin 50 has reached the end of track 52.

In the position shown in FIG. 4, actuating arm 58 has slid off bearing surface 61 and into notch 60 of fastener driver 56 so that the device as shown in FIG. 4 is ready to be fired. In this position, contacts 108 and 109 are in abutment as slider mechanism 40 has traveled further distally, thereby completing the circuit and allowing electrical current to flow from voltage source 104 to indicator 102. The indicator 102 therefore becomes lit to inform the user that the cartridge jaw is spaced a desired distance from the anvil jaw, i.e., in the proper firing range. It should be noted that the length of one or both of the electrical contacts can be modified to accommodate a range of proper firing distances. For example, if it is desired to increase the range of firing distances which cartridge 54 can be spaced from anvil jaw 20, the length (measured longitudinally) of one of the electrical contacts can be increased so that an increased number of points of contact, e.g., positions of slider 40, will complete the circuit to thereby light indicator 102.

Once in the position of FIG. 4, actuating handle 14 is moved in the direction of arrow B (FIG. 5) to fire the fasteners 66. As actuating handle 14 is moved in the direction of arrow B against the force of biasing spring 64, coupling arm 58, having been engaged in notch 60, moves in the direction of arrow C to move fastener driver 56 distally in the direction of arrow D. Fastener driver 56 drives fasteners 66 from cartridge 54 through the tissue (not shown) and into the anvil surface of anvil jaw 20. Upon completion of firing, actuating handle 14 is released and returns to the position shown in FIG. 4.

Figure 5:
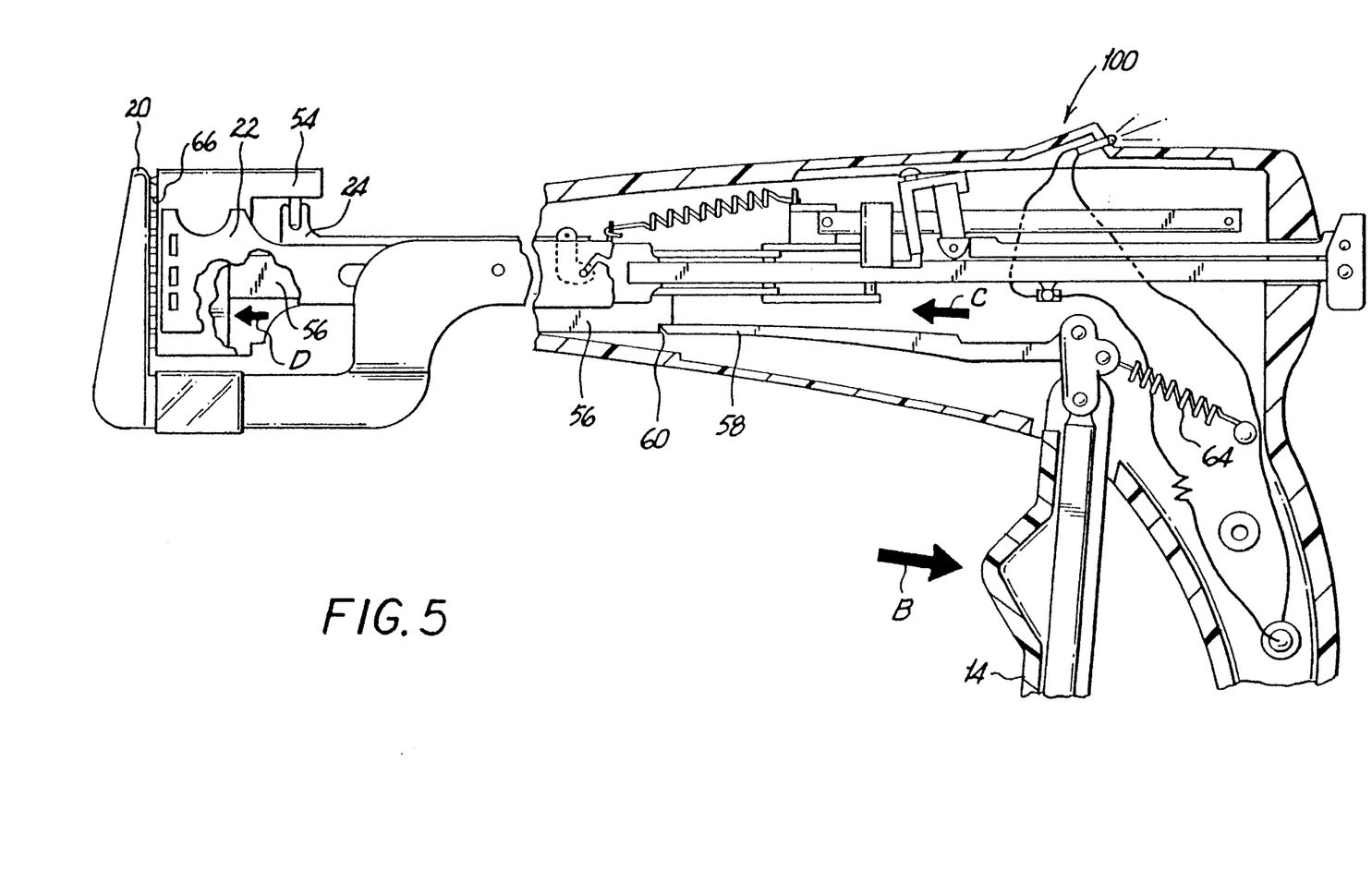
FIG. 5 illustrates the device of FIG. 2 in which the jaw mechanism is fully closed and the trigger mechanism of the device has been actuated so that the fasteners have been driven from the cartridge.
Figure 5A:
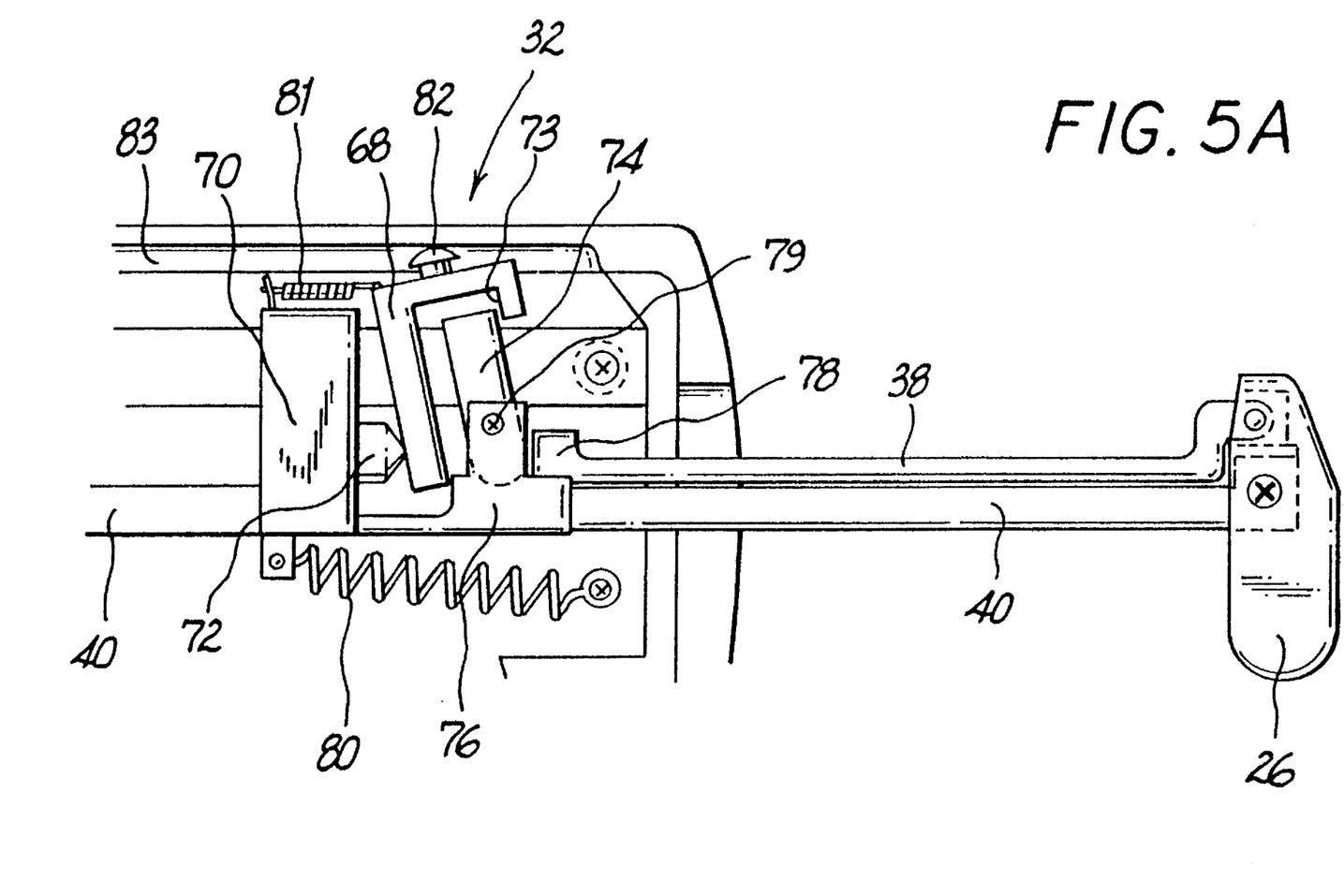
FIGS. 5A and 5B illustrate a partial enlarged view of the handle end of the device showing the release mechanism for respectively engaging and for disengaging the retaining means.
Figure 5B:
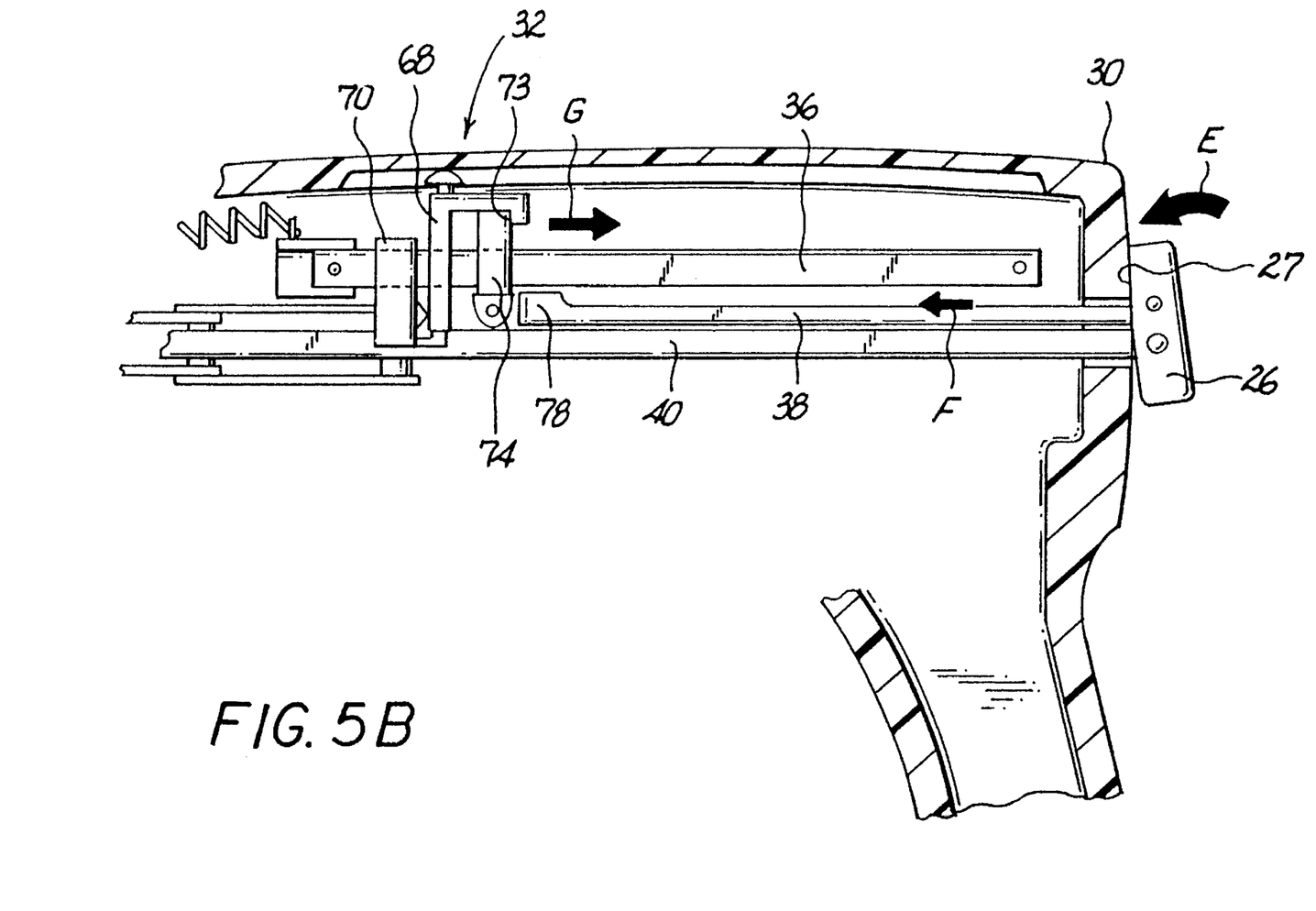

To remove instrument 10 from the surgical site, it is necessary to release the jaw mechanism 18 to return to the position shown in FIG. 2. This is accomplished by pivoting push button 26 in the direction of arrow E, as best seen in FIGS. 5A and 5B, so that beveled surface 27 contacts the housing 30. As push button 26 is pivoted in the direction of arrow E, release rod 38 travels in the direction of arrow F so that contact surface 78 of release rod 38 pivots release lever 74 as shown, which engages contact face 73 to move clamp member 68 to an upright position and perpendicular in relation to stationary rod 36. This releases the frictional engagement of clamp member 68 so that stationary rod 36 and the entire retaining mechanism 32 is moved along stationary rod 36 in the direction of arrow G due to the force of biasing spring 80. The entire mechanism, including the linkage structure 42, jaw mechanism 18, and retaining mechanism 32 is returned to the position shown in FIG. 2. The electrical contacts 109 are likewise returned to their original position of FIG. 2, thereby breaking the circuit to turn off the light indicator 102.

It should be noted that the adjustable closure mechanism described herein, can be used in other instruments to close the distance between the movable jaw member and stationary jaw member at the stapling or fastening end of the instrument or between two movable jaw members. That is the jaw mechanism may be of the type, wherein one jaw moves toward and away from the other; however, the present invention is also applicable for use with devices of alternative types, i.e., where both jaws move toward and away from each other. The surgical instrument may be of the type which applies metal staples or two part fasteners of the bioabsorbable type. The indicator device of the present invention can be used with these instruments as well.

The surgical stapling or fastening instrument employing the adjustable closure mechanism is a device which may be operated with one hand to effect the closure motion of the jaw members of the instrument followed by activation of the trigger mechanism to fire the staples or fasteners into the tissue. The complex rotational or pivoting arrangement of the prior art devices is eliminated, resulting in a lightweight and easy to handle instrument which is inexpensive to manufacture and easy to assemble.

While contacts 108 and 109 of the present invention have been shown in the handle portion of the instrument, it is within scope of the invention that the contacts may be disposed at other positions on or within the device which permits the circuit to be completed when the cartridge jaw is spaced a desired distance from the anvil jaw. For example, contact 108 may be disposed towards the distal end of the instrument and contact 109 can be secured to a movable portion of the instrument disposed at the distal portion as well. For example, contact 109 can be positioned on movable rod 34.

FIGS. 6–10 show an indicator device of the present invention utilized with a surgical stapling apparatus 111 for performing circular anastomosis. Apparatus 111 includes a handle assembly 112 having at least one pivotable actuating handle member 114, advancing means 116 and visual indicator mechanism 300. Indicator mechanism 300 includes housing 304 which supports indicator device 302. Indicator mechanism 300 functions in a manner similar to indicator 100 described above. Advancing means 116 preferably comprises a rotatable grip member 118 whose function will be described below.

Figure 6:
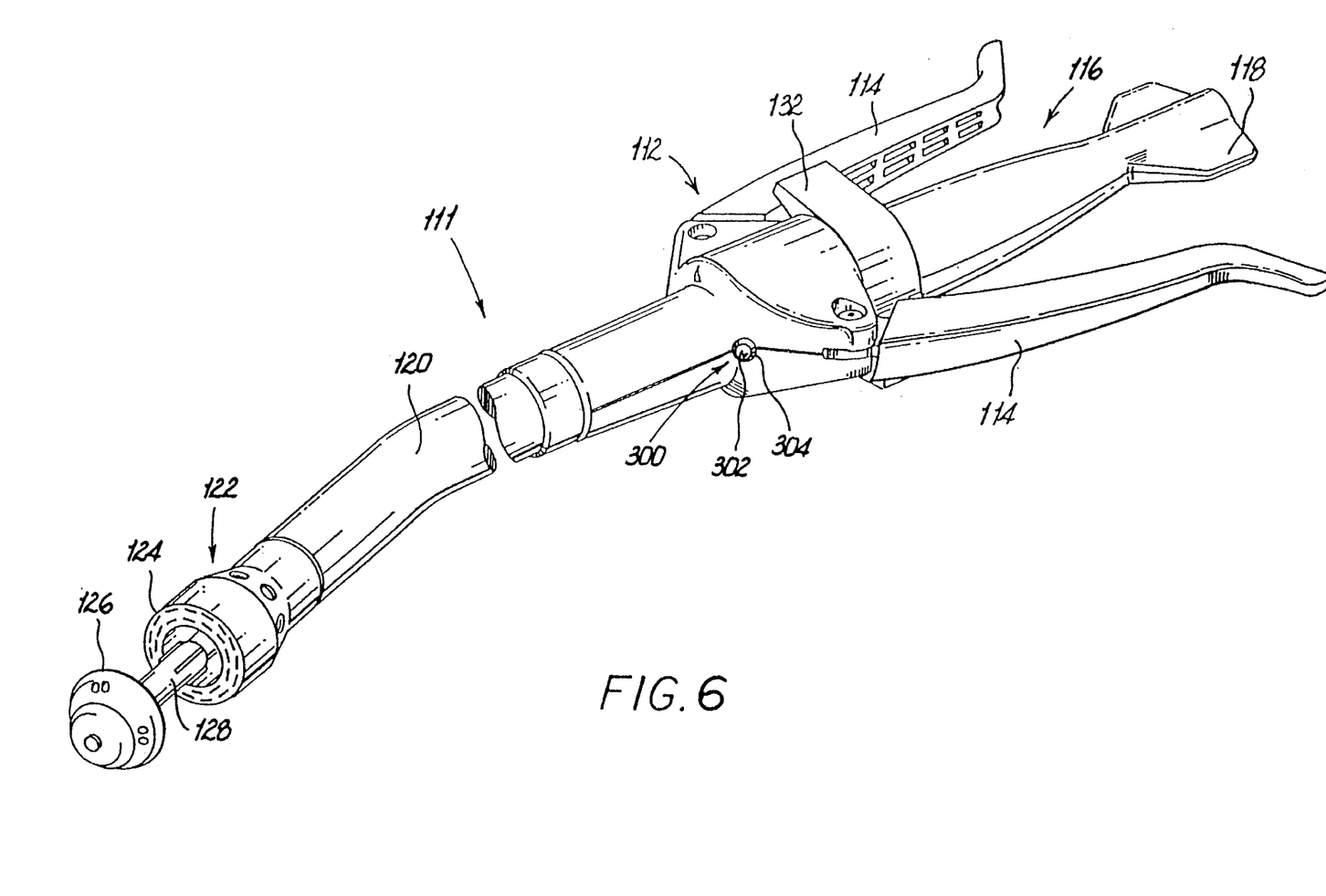
FIG. 6 illustrates a perspective view of a surgical fastening instrument for applying a circular array of fasteners including one embodiment of an indicator device of the present invention.

Extending from handle assembly 112, there is provided a tubular body portion 120 which may be constructed so as to have a curved shaped along its length. Tubular body portion 120 may also be straight, and in other embodiments may be flexible to bend to any configuration. Body portion 120 terminates in staple pusher member 122 which is associated with two annular array of staples 124. Positioned opposite staple pusher member 122 is an anvil member 126 which is connected to apparatus 111 by shaft 128. Anvil member 126 and staple pusher member 122 are disclosed in commonly assigned U.S. Pat. No. 5,119,983, issued Jun. 9, 1992, which is incorporated herein by reference.

While the preferred embodiment of the present invention utilizes a staple pusher member having an annular array of staples positioned on the tubular body portion, and having the anvil member positioned opposite the staple pusher member for movement towards and away from the staple pusher member, it is contemplated that the anvil member may be positioned on the tubular body portion and the staple pusher member and array of staples be positioned opposite the anvil member for movement towards and away from the anvil member. Such a construction is to be considered within the scope of the present invention.

Figure 7:
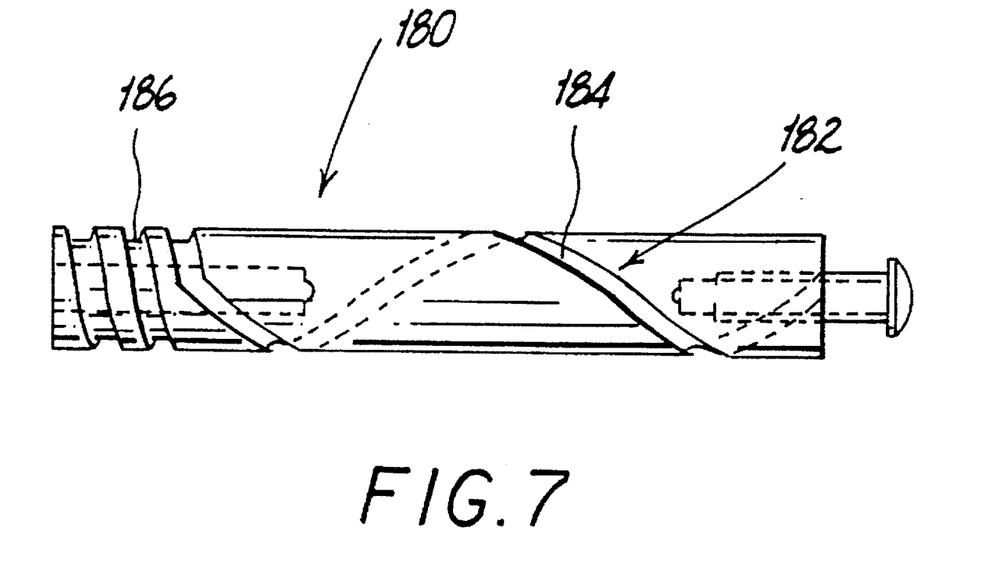
FIG. 7 illustrates a plan view of the cam member incorporated in the apparatus of FIG. 6.
Figure 8:
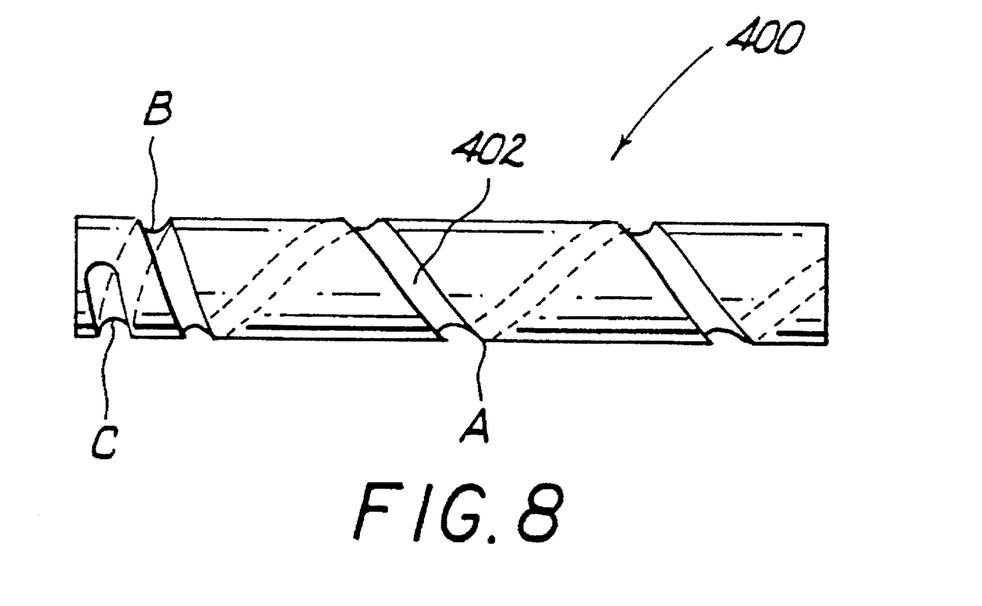
FIG. 8 illustrates an alternative embodiment of the cam member.
Figure 9:
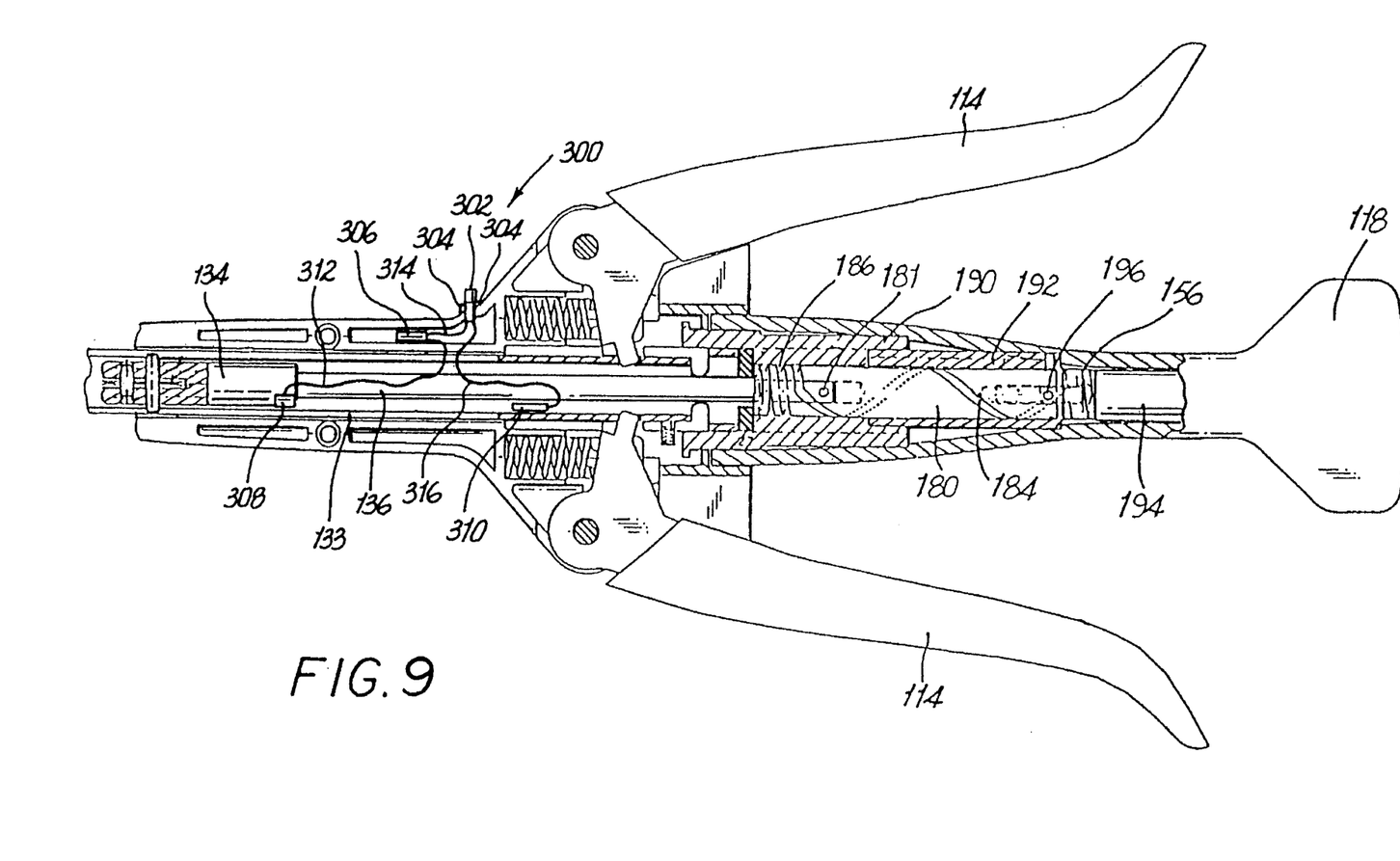
FIG. 9 illustrates a cross-sectional view of the instrument of FIG. 6 in which a cam member having a dual pitch helical groove is shown corresponding to the position where the anvil member is located away from the staple pusher member and the indicator device remains inactivated.
Figure 10:
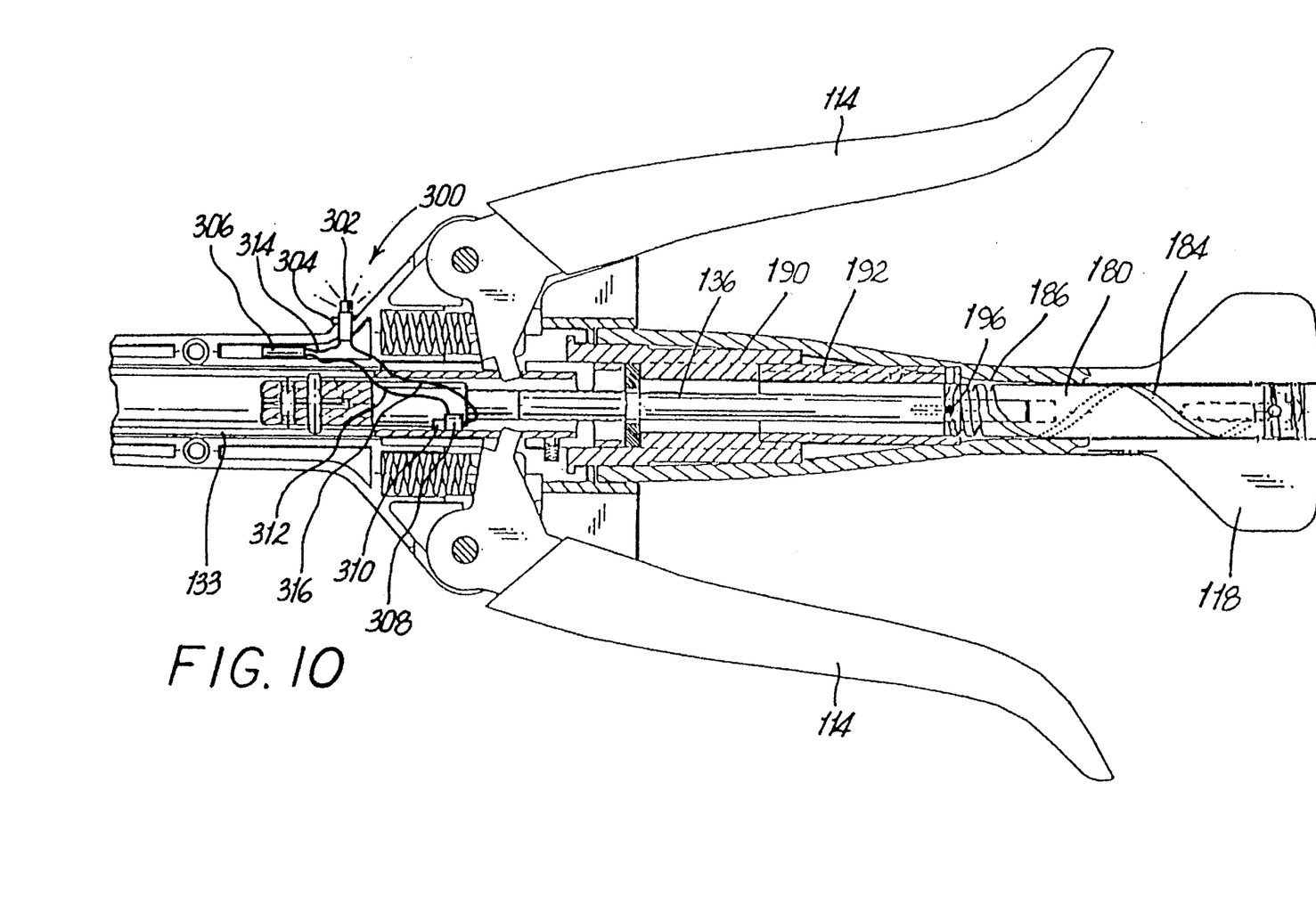
FIG. 10 illustrates a cross-sectional view of the instrument of FIG. 6 in which the cam member is shown in a position corresponding to the anvil member being positioned adjacent to the staple pusher member and the indicator device is activated.

As seen in FIGS. 7, 9 and 10, the adjustable closure mechanism includes a cam member 180 positioned within rotatable bushing 190 and rotatable sleeve member 192. Cam member 180 is provided with a helical groove 182 having a dual pitch. The first pitch 184 is greater than the second pitch 186, so that first pitch 184 provides for coarse adjustment or a large approximation of the anvil member 126 towards staple pusher member 122, while second pitch 186 provides for fine adjustment or incremental movement of the anvil member 126 towards staple pusher member 122.

In an alternative and preferred embodiment, cam 400 (FIG. 8) includes helical groove 402 having three stages of helical pitch. Stage "A" has a greater pitch than stage "B" which has a greater pitch than stage "C". As pin 196 travels along helical groove 402 (described below), longitudinal travel per revolution of the cam will vary with each stage.

Cam member 180 is secured to inner rod 136 by any suitable means to ensure that movement of cam member 138 operatively advances and retracts inner rod member 136, such as by pin 181. A rotation pin 196 is provided which is operably secured to rotatable sleeve 192, so that upon rotation of grip member 118, helical groove 182 begins to ride over pin member 196 at first pitch 184. Cam member 180 begins to slide rearwardly in bore 194, thus drawing inner rod member 136 and flexible member 134 in a proximal direction. As cam member 180 reaches a point where rotation pin 196 is at the end of first pitch 184, anvil member 126 is positioned adjacent staple pusher member 122. Further rotation of grip member 118, as seen in FIG. 10, causes second pitch 186 to ride over pin 196 to provide for fine adjustment of the distance between anvil member 126 and staple pusher member 122.

Turning to the visual indicator mechanism 300, with reference to FIGS. 9 and 10, the device includes voltage source 306, visual indicator 302, contact 310 and contact 308. Contact 308 is positioned on flexible member 134 and contact member 310 is positioned in inner tube 133. Wire position 314 electrically connects indicator 302 to voltage source 306, wire 312 connects voltage source 306 to contact 308, and wire 316 connects contact 310 to indicator 302. Clearly, alternatively, a single wire or any number of wires can be used to electrically connect these components. With reference to FIG. 10, after grip member 118 has been turned a sufficient amount, as described above, contact 308, carried by member 134 is brought into abutment with contact 310. When touching, contacts 308 and 310 complete the circuit and electrical current flows from voltage source 306 to indicator 302, thereby lighting the indicator to provide visual indication that a proper gap between anvil 126 and staples 124 has been achieved. In this embodiment, contact 310 extends in the longitudinal direction to provide for a range of contact points with contact 308. At any point where contact 308 is touching contact 310, indicator 302 will be activated and the user will be informed of adequate spacing between the anvil and stapler. Over approximation (i.e., bringing the anvil assembly too close to the staples), could result in contact 308 passing by contact 310 to a position proximal of contact 310, i.e., out of abutment so that the circuit is not closed. Therefore, indicator 300 could not only function to inform the user when the instrument has been sufficiently approximated, but can also function to inform the user when the instrument has been over approximated and the tissue potentially overclamped. While indicator 300 is shown disposed in a central portion of the instrument, it is within the scope of the invention to place the indicator at any position viewable by the surgeon or staff. Preferably, the indicator is placed in a proximal portion of the instrument, i.e., in grip member 118.

In operation, the instrument is positioned within a tubular organ in the body of the patient and the ends of the organ to be joined are positioned in the gap between the staple pusher member 122 and the anvil member 126 so that the anvil member 126 is fully extended. As is conventional, the ends of the organ may be secured over the anvil and the staple pusher member by a purse string suture prior to approximation of the anvil member in relation to the staple pusher member. In this position contacts 308 and 310 are spaced apart. In order to approximate anvil member 126 towards staple pusher member 122, grip member 118 is rotated so that helical groove 182 rides over pin member 196 causing cam member 180 to begin to move proximally. As cam member 180 moves proximally, inner rod member 136 moves proximally bringing flexible member 134 and anvil member 126 with it. This moves contact 308 proximally toward contact 310. Further movement of rod member 136 draws the anvil member 126 into position adjacent staple pusher member 122 and locates the ends of the tissue between these two members. In this position, the contacts are in abutment thereby completing the electrical circuit to activate the indicator. This will indicate to the surgeon in an easily perceivable manner that an appropriate gap between the staple cartridge and anvil has been obtained.

Note that due to the pitch of the cam member helical groove, initial rotation of grip member 118 provides for coarse adjustment of the gap or distance between anvil member 126 and staple pusher member 122 and further rotation provides for fine adjustment of the distance between the anvil member 126 and the staple pusher member 122.

Once the appropriate gap has been obtained, the surgeon squeezes handles 114 to fire the instrument. Movement of handles 114 towards the body of the instrument causes inner tube 133 to move in a distal direction, thereby causing staples 124 to be ejected from pusher member 122. When ejected, staples 124 pass through tissue disposed between pusher member 122 and anvil 126 and are formed to a tissue securing configuration upon contacting depressions (not shown) in anvil 126. After firing, the instrument is removed in a manner known in the art.

Other embodiments of the circular anastomosis insert instrument as well as the detailed operation are disclosed in commonly assigned copending U.S. patent application Ser. No. 07/959,275 filed Oct. 10, 1992, the entire contents of which is incorporated herein by reference.

Figures 11, 11A:
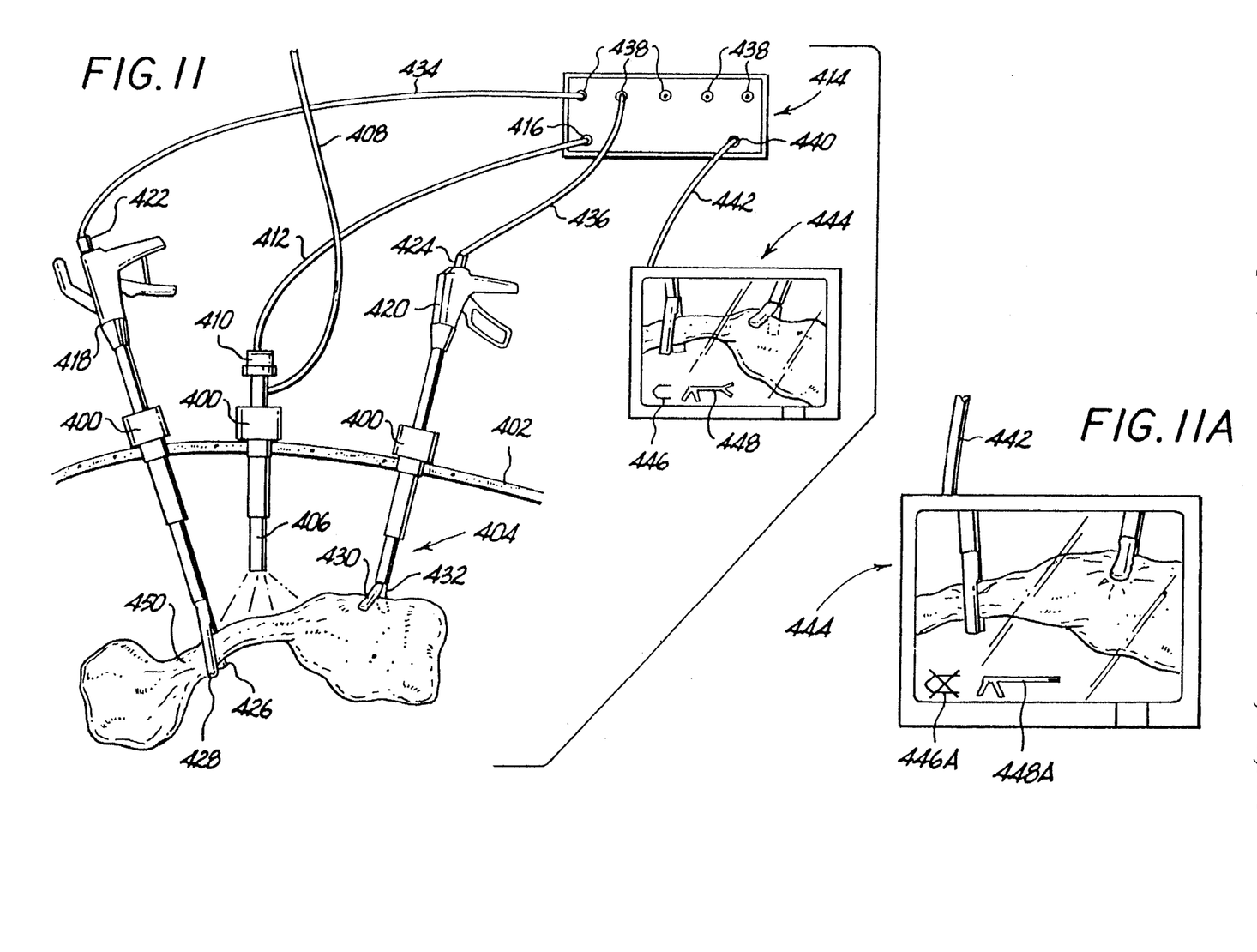
FIGS. 11 and 11A are schematic illustrations of an alternative embodiment of the present invention.

Turning to a further alternative embodiment of the present invention, FIG. 11 shows schematically a system whereby data is transmitted to a video monitor for display, such data relating to the position and/or condition of one or more surgical instruments. As shown in FIG. 11, a laparoscopic surgical procedure is being performed wherein a plurality of trocar sleeves 400 are inserted through a body wall 402 to provide access to a body cavity 404. A laparoscope 406 is inserted through one of the trocar sleeves 400 to provide illumination (light cable 408 is shown leading toward a light source, not pictured) to the surgical site and to obtain an image thereof. A camera adapter 410 is attached at the proximal end of laparoscope 406 and image cable 412 extends therefrom to a control box 414 discussed in more detail below. Image cable inputs to image receiving port 416 on control box 414.

Additional surgical instrumentation 418, 420 are inserted through additional trocar sleeves 400 which extend through body wall 402. In FIG. 11, instrument 418 schematically illustrates an endoscopic stapling device, e.g., an Endo GIA* instrument manufactured by the assignee of this application, and instrument 420 schematically illustrates a hand instrument, e.g., an Endo Grasp* device also manufactured by the present assignee. Additional and/or alternative instruments may also be utilized according to the present invention; the illustrated instruments are merely exemplary of surgical instruments which may be utilized according to the present invention.

Instruments 418, 420 include adapters 422, 424 associated with their respective handle portions. The adapters electronically communicate with conductive mechanisms (not pictured) of the type described hereinabove with respect to the embodiments of FIGS. 1–10. These mechanisms, which include electrically conductive contact members electrically connected by wires, cables and the like, are associated with the distal elements of the respective instruments, e.g., the anvil 426 and cartridge 428 of the Endo GIA* instrument, the jaws 430, 432 of the Endo Grasp* device, and the like. The mechanisms are adapted to interrupt an electronic circuit when the distal elements are in a first position or condition and to complete the electronic circuit when the distal elements are in a second position or condition. A voltage source for the electronic circuit may be provided in the surgical instrument, e.g., in the form of a battery, or supplied from control box 414 through cables 434 and 436.

Control box 414 includes a plurality of jacks 438 which are adapted to receive cables 434, 436 and the like. Control box 414 further includes an outgoing adapter 440 which is adapted to cooperate with a cable 442 for transmitting the laparoscopic image obtained by the laparoscope 406 together with data concerning surgical instruments 418, 420 to video monitor 444. Circuitry within control box 414 is provided for converting the presence of an interrupted circuit, e.g., for the electronics within cable 434 and the mechanism associated with the distal elements of instrument 418, to an icon or symbol for display on video monitor 444. Similarly, the circuitry within control box 414 is adapted to provide a second icon or symbol to video monitor 444 when a completed circuit exists for cable 434 and the associated mechanism.

Illustrative icons/symbols 446, 448 are shown on video monitor 444. Icon 446 shows a surgical staple and could be used to communicate to the surgeon that the cartridge 428 and anvil 426 of instrument 418 are properly positioned to form staples in tissue 450. Icon 446 could take another form when the cartridge 428 and 426 are not properly positioned for forming staples, thereby interrupting the circuit, e.g., as shown in FIG. 11A. Icon 448 shows a hand instrument with jaws spread apart, thereby communicating to the surgeon that the jaws 430, 432 of instrument 420 are open. Icon 448 could take another form when jaws 430, 432 are closed, thereby completing the circuit, e.g., as shown in FIG. 11A.

As will be readily apparent to one of ordinary skill in the art from the disclosure herein, alternative icons/symbols and/or display indicia may be utilized to communicate to the surgeon the position/condition of surgical instruments utilized according to the present invention, e.g., flashing icons, variable color icons, repositioned icons. Regardless of the type of icon/symbol/indicia selected, the presence of the icons/symbols/indicia on the video monitor permit the surgeon to easily and conveniently ascertain the position/condition of a surgical instrument while viewing the video monitor on which the progress of the surgical procedure is being displayed. The surgeon may also, at his or her election, disconnect the cables from the surgical instruments, thereby disabling the icon/symbol/indicia system, without effecting the operation of the subject surgical instrument.

While the invention has been particularly shown and described with reference to the preferred embodiments, it will be understood by those skilled in the art that various modifications and changes in form and detail may be made therein without departing from the scope and spirit of the invention. For example, while the electrical circuit for the above-described instrument have been described in terms of wires, it is understood that any method of transferring electrical current between the voltage source and visual indicator is within the scope of the present invention. In this regard, for example, the electrical path can be defined by conductive materials coated or plated on the handle, body, or movable parts. Other electrically conductive materials include bonded wires and flex cables. The electrical curcuit can be completed in any known mannner, including, for example, the use of magnets, reed switches etc. Furthermore, multiple indicators can be used to indicate different events such as the proper placement of a staple cartridge, the firing of the instrument, etc.

Similarly, the transfer of the electronic data from the surgical instrument to the control box may be accomplished by a transmitter associated with the surgical instrument and a receiver associated with the control box, thereby obviating the need for a cable extending therebetween. In a transmitter/receiver embodiment, a voltage source is required within the surgical instrument to power the circuitry and the transmitter.

The voltage source is preferably a battery, and most preferably a lithium battery. However, other sources of electrical current are considered to be within the scope of the present invention, i.e., photo voltaic cells, external plugs, and the like. Accordingly, modifications such as those suggested above, but not limited thereto, are to be considered within the scope of the invention.

What is claimed is:

1. A system for performing surgery, comprising:

a control box which includes internal circuitry;

a surgical instrument including a distal element and means for sensing a position or condition of said distal element;

means associated with said surgical instrument for transmitting said sensed position or condition to said internal circuitry of said control box; and means for transmitting said sensed position or condition from said internal circuitry of said control box to a video monitor for display thereon, wherein said sensed position or condition is displayed on said video monitor as an icon or symbol, further comprising a voltage source for generating a voltage contained entirely within said surgical instrument.

2. The system as recited in claim 1, further comprising an endoscope or laparoscope for obtaining an image of a surgical site, wherein said control box further comprises means for receiving said image from said endoscope or laparoscope and transmitting said image to said video monitor.

3. A system as recited in claim 1, wherein said means for transmitting to said control box is a cable.

4. A system as recited in claim 1, wherein said means for transmitting to said control box is a transmitter associated with said surgical instrument and receiving means associated with said control box for receiving transmissions from said transmitter, said voltage source providing power to said transmitter.

5. A system as recited in claim 1, wherein said icon or symbol is displayed in color.

6. A system as recited in claim 1, wherein said icon or symbol flashes on said video monitor.

7. A system as recited in claim 1, wherein said distal element contains a surgical staple.

8. A system as recited in claim 1, wherein said voltage source is a battery.

9. A system as recited in claim 1, wherein said icon or symbol depicts a surgical instrument.

10. A system for performing surgery, comprising:

i) a surgical apparatus having a housing and a tool mechanism extending from said housing, said tool mechanism being movable from a first position to a second position;

ii) means for generating a first signal when said tool mechanism is in said second position; and iii) means for transmitting said first signal to a video monitor remote from the surgical apparatus, said sensed position or condition being displayed on said video monitor as an icon or symbol, further comprising a voltage source for generating a voltage contained entirely within said surgical instrument.

11. A system as recited in claim 10, wherein said icon or symbol is displayed in color.

12. A system as recited in claim 10, wherein said icon or symbol flashes on said video monitor.

13. A system as recited in claim 10, wherein said icon or symbol depicts said tool mechanism.

14. A system as recited in claim 10, wherein said tool mechanism contains a surgical staple.

15. A system as recited in claim 10, wherein said voltage source is a battery.

16. A system as recited in claim 10, wherein said icon or symbol depicts a surgical instrument.

* * * * *